(12) United States Patent
Auer et al.

(10) Patent No.: US 6,258,549 B1
(45) Date of Patent: *Jul. 10, 2001

(54) ELISA SCREENING METHOD FOR INHIBITORS OF HUMAN IGE BINDING TO THE HIGH AFFINITY RECEPTOR, FCεRIα

(75) Inventors: Manfred Auer, Mödling; Franz Hammerschmid; Georg Stingl, both of Vienna, all of (AT)

(73) Assignee: Novartis AG, Basel (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/101,053

(22) PCT Filed: Dec. 23, 1996

(86) PCT No.: PCT/EP96/05824

§ 371 Date: Sep. 25, 1998

§ 102(e) Date: Sep. 25, 1998

(87) PCT Pub. No.: WO97/24617

PCT Pub. Date: Jul. 10, 1997

(30) Foreign Application Priority Data

Dec. 28, 1995 (GB) .................................................. 9526599

(51) Int. Cl.[7] ..................... G01N 33/53; G01N 33/564; G01N 33/567; G01N 33/568

(52) U.S. Cl. ..................... 435/7.1; 435/7.24; 435/7.5; 436/506; 436/513; 436/538; 436/541

(58) Field of Search ..................... 435/77.24, 7.5, 435/969, 971; 436/506, 513, 538, 541

(56) References Cited

U.S. PATENT DOCUMENTS

| | | | |
|---|---|---|---|
| 4,935,339 | * 6/1990 | Zahradnik | 435/5 |
| 4,962,035 | 10/1990 | Leder et al. | 435/320 |
| 5,639,660 | 6/1997 | Kinet et al. | 435/252.3 |
| 5,714,338 | * 2/1998 | Wai-Fei | 435/7.24 |

FOREIGN PATENT DOCUMENTS

| | | |
|---|---|---|
| 0 507 586 | 10/1992 | (EP) . |
| WO 94/11734 | 5/1994 | (WO) . |
| WO 95/16203 | 6/1995 | (WO) . |
| WO 96/01643 | 1/1996 | (WO) . |

OTHER PUBLICATIONS

Ra, C, et al., Soluble human high affinity receptor for IgE abrogates the IgE–mediated allergic reaction. Int. Immunol. 5(1):47–54, 1993.*

Derwent Abstract, 95–149749/20 (JP 07 072 150—Mar. 17, 1995).

Derwent Abstract 85–012102/02—WO 8404–970, Dec. 20, 1984.

Derwent Abstract 85–117732/20, EP 141,581, May 15, 1985.

Derwent Abstract 90–126548/17, EP 365,449, Apr. 25, 1990.

(List continued on next page.)

Primary Examiner—David Saunders
Assistant Examiner—Mary Beth Tung
(74) Attorney, Agent, or Firm—David E. Wildman; Gregory D. Ferraro

(57) ABSTRACT

The present invention is directed to an Assay for high capacity screening of substances interfering with the attachment of human IgE to its high affinity receptor and/or of substances capable of detaching already bound IgE from this receptor and for the differential analysis between autoimmune disorders and classical allergies.

4 Claims, 10 Drawing Sheets

OTHER PUBLICATIONS

Derwent Abstract 90–164005/21, WO 9004–609, May 3, 1990.
Derwent Abstract 90–044742/06, US 4,885,172, Dec. 05, 1989.
Derwent Abstract 90/000604/01, DE 3,820,556, Dec. 21, 1989.
Derwent Abstract 90–038598/06 EP353 895, Jul. 2, 1990.
Derwent Abstract 89–257471/36 EP331127, Sep. 6, 1989.
Medline Abstract 88285777, Journal of Immunological Methods, (1988) 111(2) 271–275.
Derwent Abstract 94–318470/40, EP 620438, Oct. 19, 1994.
Derwent Abstract 90–059264/08, US 7,351,042, Dec. 12, 1989.
Derwent Abstract 90–336580/45EP 396116, Nov. 7, 1990.
Derwent Abstract 90–344171/46, JO 2247564, Oct. 3, 1990.
Derwent Abstract 90–225833/30, EP379216. Jul. 25, 1990.
Derwent Abstract 91–119202/17, EP 423,938, Apr. 24, 1991.
HCAPLUS Abstract 1991:38729, Haun et al., Anal.kBiochem. (1990), 191(2), 337–42.
HCAPLUS Abstract 1991:12124, Loughrey et al., J. Immunol. Methods (1990), 132(1), 25–35.
HCAPLUS Abstract 1991:605327, Immonol. Lett. (1990), 26(3), 283–284.
Derwent Abstract 91–304838/42, EP 451,800, Oct. 16, 1991.
Derwent Abstract 92–333803/41, EP 507587, Oct. 7, 1992.
Derwent Abstract 93–145413/18, EP 540037, May 5, 1993.
Derwent Abstract 93–076536/09, WO 9303181, Feb. 18, 1993.
Derwent Abstract 94–092329/11, US 5,296,347, Mar. 22, 1994.
Medline Abstract 94304968, Yan et al., Bioconjugate Chemistry, (1994 Mar–Apr) 5 (2) 151–7.
Derwent Abstract 95–006821/01, WO9426934, Nov. 24, 1994.
HCAPLUS Abstract 1993:122513, Olivieri et al., J. Immonol. Methods (1993), 157(1–2), pp. 65–72.
HCAPLUS Abstract 1993–552919, Wainwright et al., Am. Biotechnol. Lab. (1993), 11(7), 52, 54.
HCAPLUS Abstract 1994:116527, Loughery et al., Liposome Technol. (2nd Ed.) (1993), vol. 3, pp. 163–178.
HCAPLUS Abstract 1993, 576061, Fein et al., J. Membr. Biol. (1993), 135(1), 83–92.
Derwent Abstract 95–256022 [34] AU 9458829 Aug. 1, 1995.
Derwent Abstracts, 95–216818/29, EP 657,737, Jun. 14, 1995.
Derwent Abstract, 95–240615/31, WO 95127427, Jun. 29, 1995.
Derwent Abstract, 96–231449/24, DE 4439452, May 9, 1996.
HCAPLUS Abstract 1984:628187. J. Immunol. Methods (1984), 73(1), 83–95.
Derwent Abstracts, 96–161769/17, EP 703452, Mar. 27, 1996.
Derwent Abstract, 95–312310/41 DE4407423, Aug. 7, 1995.
Yoshikawa, T. et al., Immunomethods, vol. 4, pp. 65–71 (1994).
Fiebiger, E. et al., Journal of Clinical Investigation, vol. 96, pp. 2606–2612 (1995).
Hide, M. et al., N. Engl. Journal of Med., vol. 328(22), pp. 1599–1624 (1993).
Maurer, D. et al., J. Immunol., vol. 154, pp. 6285–6290 (1995).
Technical Information Sheet, Genosys Biotin Streptavidin Capture Microcolumns—Affinitip™—http://www.genosys.com/prods/biotin.ht (Dec. 3, 1996)—2 pages.
Wang, B. et al., J. of Experimental Medicine, vol. 175, pp. 1353–1365 (1992).

* cited by examiner

ELISA SCREENING METHOD FOR INHIBITORS OF HUMAN IGE BINDING TO THE HIGH AFFINITY RECEPTOR, FCεRIα

CROSS REFERENCE TO RELATED APPLICATIONS

This is a 371 of PCT/EP96/05824, filed Dec. 23, 1996.

FIELD OF THE INVENTION

The invention relates to a test system by ELISA (enzyme-linked immunosorbent assay). It concerns an ELISA system to detect biochemical entities in very minute amounts and in the presence of structurally very similar compounds, which are differentiated by means of monospecific antibodies, such as immunoglobulins of various species.

DESCRIPTION OF THE RELATED ART

In conventional ELISA systems either the antigen which is to be detected, or a specific antibody which binds to the respective antigen, is bound to a solid phase (microtiter plate) by hydrophobic interactions: the protein interacts with the solid phase, usually a polystyrene surface at high pH. Although this bond is responsible for all the consecutive steps in the procedure, it remains the weakest bridge to the assay support, the ELISA plate. Strong detergents at higher concentrations such as 0.05% are able to diminish the amount of reagent bound to the plate and can even abolish binding totally. The consecutive steps in ELISA technique, such as the binding of an antigen to the solid phase-bound antibody and further binding of a second antibody, occur with an affinity of approximately $10^{-12}$ to $10^{-10}$ mol per liter. One can view this as being similar to an inverse binding cascade from the bottom of the plate to the top, as with a pyramide standing on its top.

Another concern is the intramolecular event upon binding. A protein such as a cell-receptor or an antibody behaves very flexibly according to its polypeptide structure, which forms, a complex architecture in solution. This explains its high specificity and selectivity to the ligands which are to bind to it in vivo. Enzymatic activities for example are entirely dependent upon the proper formation of the active site pocket, which itself remains flexible in order to engulf the substrate and release the product. Cell-receptors such as FcεRIα react with an affinity for IgE in vivo of $10^{-10}$ mol per liter provided the respective active site is properly exposed. Most proteins react to binding to a given surface with a dramatic change of their tertiary structure, i.e. they unfold, refold, hide their active site or change their conformation in such a way that their reactivity toward a given ligand is altered or even cancelled. In order to circumvent this disadvantage, in conventional ELISA systems a catching antibody is used. This antibody binds to the polystyrene plate and exposes the high affinity hyper-variable region toward the incoming antigen. The antigen is then detected by a second antibody, which is labelled directly or indirectly (via biotin/avidin) with an enzyme. This enzyme will cleave a chromogenic substrate, which itself is converted from the leucoform to the chromoform and thus visualizes the presence of the antigen in question. But even catching antibodies may affect a given protein by changing its conformation. This is demonstrated by many examples of therapeutic antibodies whose mode of action is the blocking of an active site on, or the alteration of, a biospecific molecule.

SUMMARY OF THE INVENTION

The present invention concerns an assay for high capacity screening of substances interfering with the attachment of human IgE to its high affinity receptor FcεRIα, and/or of substances capable of detaching already bound IgE from this receptor, which is devoid of the above disadvantages. It comprises reacting a solution of a biotinylated FcεRIα receptor with IgE, transferring the resultant binding reaction mixture to a streptavidin-coated plate and quantifying by means of an appropriate enzyme-labeled antibody. More specifically, it comprises reacting biotinylated IgE-receptor with IgE in the presence or absence of interfering or inhibitory substances, such as non-biotinylated IgE-receptor at well-defined molar concentrations, temperature, pH and salt conditions, thereby eliminating the structural influence of solid phases, and transferring after a defined incubation time an aliquot of the binding reaction mixture to a streptavidin-coated multiple well plate, where the biotinylated IgE-receptor/IgE complex is quantified by means of an appropriate enzyme-labeled antibody, such as horse radish peroxidase (POD)-labeled antibody against human IgE.

DESCRIPTION OF THE PREFERRED EMBODIMENTS

The principle of this assay method is as follows: biotinylated IgE-receptor is first reacted with IgE in the presence or absence of interfering or inhibitory substances, such as non-biotinylated IgE-receptor, at well-defined molar concentrations, temperature, pH and salt conditions, thereby eliminating the structural influence of solid phases. After a defined incubation time an aliquot of the binding reaction mixture is transferred to a streptavidin-coated multiple well plate, where the biotinylated IgE-receptor/IgE complex is trapped and quantified by means of an appropriate enzyme-labeled antibody, such as horse radish peroxidase (POD)-labeled antibody against human IgE.

During the reaction of the receptor with its ligand (IgE) in solution, both molecules float freely in solution and thus are not influenced by the structural modification of solid phases. They receive their conformation by the given pH and salt concentration and exert their maximal binding affinity. After a given incubation time, selected according to the results of appropriate equilibrium measurements, the receptor/ligand complex has to be deprived of all other compounds. The receptor is therefore biotinylated prior to the above reaction and an aliquot of the reaction is transferred to a streptavidin-coated multiple well plate. In order to build up an affinity cascade from the bottom of the multiple well plate to the top of the reactants, the binding of streptavidin with the plate surface is preferably made covalent. For example, a microtiter plate (such as a DNA-Bind plate) chemically modified with e.g. a N-oxysuccinimide ester coating is used, which reacts with nucleophiles such as primary amines under formation of a covalent bond. This bond is stronger than $10^{-15}$ moles per liter. For the next step, the biotinylation of the receptor, a chemically modified biotin, such as NHS-LC-Biotin is used, which comprises an extended spacer arm of approximately 22.4 Å in length. This long chain analogue reduces steric hindrances associated with the binding of four biotinylated molecules on one streptavidin molecule. The target of biotinylation on the IgE-receptor molecule is thereby well defined and interference with the ligand is avoided. The binding affinity of biotin to streptavidin is also known to be $10^{-15}$ moles per liter. Thereby the first two steps of the binding cascade are established and reach from the bottom of the plate to streptavidin to the biotinylated receptor. The affinity constants are decreasing from the bottom to the top. At this stage the reactants, which have found their partners in solution under appropriate conditions, are trapped by the means of the streptavidin plate, and the bound IgE is then detected with an appropriate enzyme-labeled antibody, such as POD-labeled antibody against human IgE. The affinity cascade now reaches from $<10^{-15}$ to $10^{-15}$ to $10^{-10}$ to $10^{-12}$ for the anti-IgE antibody toward IgE. Any interference of biochemical material and especially of IgE-receptor binding inhibitors will occur at the point with the lowest affinity, which resides between the IgE and the receptor ($10^{-10}$), and not at the point of attachment of the assay to the plate. This would be read as a false positive result—an artifact of the system.

The above provides the basis for the detection of biomolecules other than IgE but which are also binding to FcεRIα. The prerequisite therefor is the abolishment of the binding of IgE to the receptor in order to keep the receptor site free for other molecules. This is achieved by means of an anti-IgE antibody as BSW17 which binds to the receptor-binding site of the IgE and thus renders the molecule non-effective, whereby even in the presence of IgE other biomolecules can bind to the IgE-binding site of the receptor (the hybridoma cell line producing monoclonal antibody BSW17 has been deposited on Dec. 18, 1996 with the European Collection of Animal Cell Cultures (ECACC), Porton Down, U.K. under the provisions of the Budapest Treaty on the deposit of microorganisms, under deposit No. 96121916).

More particularly, the invention concerns an ELISA-type assay for finding inhibitors of the binding of human IgE to its high affinity receptor, the α-chain of FcεRI (FcεRIα), especially substances inhibiting IgE-mediated early phase response in allergic reactions. The assay mimics natural conditions of binding of IgE to its receptor, i.e. all binding partners interact in solution instead of one of them being immobilized on a solid support. In the binding reaction biotinylated soluble FcεRIα chain interacts with free, soluble IgE at a defined molar ratio (1:2.5) in the presence of inhibitory or interfering substance to reach thermodynamic equilibrium within a three-hours incubation period at 37° C. The IgE/FcεRI complex formed under these conditions is captured via the biotin-linker coupled to the FcεRIα chain on ELISA plates modified by covalently-linked streptavidin. The amount of captured complex is determined by identifying bound IgE via a peroxidase-linked anti-human IgE antibody preparation, such as anti-human IgE (ε-chain-specific) peroxidase conjugates e.g. Sigma no. A-9667. The concentrations of the binding partners in primary screening are chosen to obtain an optimal signal to noise ratio under nonsaturating conditions. In this experimental setting the $K_d$ of the IgE/FcεRI complex formed is found to be 4 nM. The maximally tolerated dose of DMSO in the test solution is 5% and therefore, at a concentration of pure compound of 50 μM competitive inhibitors with a $K_d$ of 30–10 μM can be easily detected in primary screening at a cut-off level of 30% inhibition. As a standard control a monoclonal antibody recognizing free as well as receptor-bound IgE and inhibiting its binding to the receptor or releasing it from the complex, respectively, such as BSW17, is tested in 5 different concentrations on every screening plate.

Some of the advantages of this assay in comparison to standard ELISA systems where the receptor or antigen first will be attached to a solid support with either a catching antibody or by high pH (9.6) are the following:
1. The structural influence by the supporting solid phase or the catching antibody in standard sandwich-ELISA is avoided;
2. no treatment of the receptor or antigen at alkaline pH;
3. defined molar concentrations of the reaction partners; and
4. reduced working steps and easy handling by robotics.

Allergies in their major manifestations, known as asthma, allergic rhinitis or atopic dermatitis, afflict more than 20% of the population in industrialized countries. They are generally caused by an overproduction of IgE in genetically predisposed individuals in response to common environmental antigens. The high affinity receptor for IgE, the multimeric FcεRI present on mast cells, basophils, human Langerhans cells and monocytes of allergic individuals, mediates immediate hypersensitivity responses if aggregated by IgE/allergen complexes. Therefore, to interfere with the binding of IgE to FcεRI is a major new strategy for alternative treatment of allergic patients. Several approaches in this direction are already in early clinical evaluation or in preclinical development, such as the use of blocking antibodies against IgE, of recombinant soluble FcεRI α-chain, or of inhibitory peptides. In view of the well-known drawbacks of such approaches, such as potential immunogenicity, poor bioavailability and high treatment costs, low molecular weight compounds inhibiting this crucial interaction in allergic response are needed. As the affinity of IgE toward FcεRI is high ($K_a=10^{10}$ M$^{-1}$) a low hit-rate in any sample collection is expected. However, the throughput of test samples in the above assay can be very high (>1000 samples/day) and the sensitivity is also high, as compounds which competitively inhibit the binding reaction with a $K_d$ of 10 μM are easily detected by a signal reduction of 50%.

Further, the soluble extracellular part of the α-chain, the IgE-binding subunit of FcεRI, is available through recombinant DNA technology and hence the assay for high capacity screening of inhibitors of the IgE/FcεRI interaction could be established cell-free. To mimic the natural binding reaction of IgE to the α-chain the assay is designed for the interaction of binding partners to occur in solution. Instead of directly immobilizing one binding partner on a solid support by non-covalent adsorption techniques, e.g. the α-chain by hydrophobic interactions on the surface of ELISA plates, an interaction which is highly susceptible to detergent-like substances, a more stable form of fixation to the solid medium is evaluated. The affinity of biotin for streptavidin is orders of magnitude higher ($K_d$ approximately $10^{-15}$ M) than that of IgE for FcεRI. Therefore, inhibitors of the IgE/FcεRI interaction are unlikely to disturb the interaction of biotin and streptavidin. Additionally, the latter is insensitive to extremes of pH. Hence, this interaction was chosen to capture the IgE/α-chain complex on the surface of ELISA plates. For this purpose, the α-chain is biotinylated using an extended spacer arm for chemical coupling and streptavidin is covalently bound to the ELISA plate via amino groups. The binding reactions between IgE and its high affinity receptor, FcεRIα, and the interference of test compound are performed in a separate multiple well plate to reach the equilibrium in solution during an extended incubation period at 37° C. To favor conditions for inhibitory compounds to be active, they are added to and preincubated with the α-chain prior to the addition of IgE. The residual IgE/α-chain complex formed in the presence of test compound is then captured on the streptavidin plate during a short incubation period at room temperature or alternatively, after an overnight incubation at 4° C. The amount of captured complex is determined by a peroxidase-catalyzed colorimetric reaction using an anti-human IgE antibody preparation with covalently coupled enzyme.

The key steps of the assay are schematically presented in FIG. 1. The following Example illustrates the invention but is not limitative thereof.

EXAMPLE

Assay Procedure

1. Preparation of Covalently-Bound Streptavidin Microtiter Plates

To 12 ml of PBSdef. PH9, 6 µl of streptavidin solution is added and the mixture is stirred for a few minutes [1 µg/ml]. 100 µl of this solution are pipetted into each well of a Costar Amine plate, which is taken directly from 4° C. storage and dismantled from its protective envelope prior to pipetting. The whole procedure is performed in the dark and the plate must be kept in a light protective aluminium foil for 1 hour at room temperature. Thereafter, the consecutive steps can be done under normal conditions: five washes (Biomek) of the plate with PBST and tapping onto a paper towel in order to free the plate from residual moisture, addition of 360 µl of 0.5 M Tris-Cl pH 8 and incubation for 1 hour at room temperature. This step will inactivate residual free ester groups on the plate surface. Then, 200 µl of blocking solution (2% BSA in PBS, 0.05% Tween 20) is added into each well and kept at room temperature for 30 minutes. Then the plate is washed once more as described and stored in a sealed plastic box at 4° C.

2. Biotinylation of the FcεRIα Receptor

A given amount of receptor solution (FcεRIα, extracellular portion, recombinant, produced in insect cells) is concentrated by ultrafiltration over Amicon YM 3/25 to give 1.5 ml at a concentration of 2.2 mg protein per ml. This solution is dialyzed with a Pierce SLIDE-ALYZER against three times 1 liter of 100 mM sodium carbonate pH 8.5 within four hours at 4° C. The biotinylation is done by adding 23 µl of a solution of 4.8 mg of Biotin II Pierce in 120 µl of DMF and the vial is tumbled for 15 minutes at room temperature. After another addition of 23 µl of the biotin solution the whole device is transferred to 4° C. and tumbling continued for 1.5 hours. Then the reaction is stopped by addition of 150 µl of 1 M Tris-Cl pH 8 and a further incubation for 10 minutes at room temperature.

3. Column-Chromatography

This sample is loaded onto a FPLC Superdex 75 [16× 1200 mm] in PBS 0.02% sodium azide at 4° C. The flow-rate is 2 ml/min, the fraction size is 2.6 ml. The fractions containing adequately biotinylated receptor are pooled and concentrated over an Amicon YM 3/43 to approximately 4 ml. After determination of the protein concentration an equal volume of glycerol is added. 100 µl aliquots of this solution are stored at −80° C. 50 µl of fraction aliquots are placed into each well of a streptavidin-covalent-plate and kept at room temperature for one hour. Thereafter the plate is washed with PBST and 50 µl of IgE [20 nM] are added to each well and incubated for one hour at room temperature. After a subsequent wash with PBST, 100 µl of anti-IgE-POD [1:1000] are added to each well and the plate is further incubated for one hour. Then the plate is washed again and 100 µl of TMB substrate are added. After 20 minutes of incubation at room temperature the reaction is stopped by addition of 100 µl of 4 N $H_2SO_4$ and the plate is read at 450 nm.

A high molecular weight pool is detected containing highly biotinylated but aggregated material, which binds to the plate but consequently is inactive in binding to IgE. The appropriate IgE-binding competent material is found at the expected elution position of 32 kDa. Remaining reactants are seen in a low molecular weight fraction as well.

4. Screening

All substances to be tested are distributed into multiple well plates for testing in solutions of 10 mM NaCl; 50% DMSO at a concentration of 200 µg/ml or 500 µM. These solutions in conical bottom plates are diluted once more 1:3.3 (20 µl of substance plus 46 µl of incubation buffer) into round-bottom plates to give 66 µl of 150 µM substance in 15% DMSO. These plates are adjusted in position A4–A12 by emptying the wells by suction (the whole line A1–A3 is dedicated for medium references=High control) and 2 M NaOH is pipetted into wells A9–A12 in order to give the Low control. IgG BSW17 is pipetted into well A4–A8 at 12 nM in two-fold dilutions. These are the dilution plates. Then the working solution for the receptor is prepared by diluting the stock solution to 600 pM in incubation buffer. 50 µl of this solution is distributed to each well of a new round bottom plate (incubation plate) and 50 µl of the respective dilution plate is transferred to this plate and mixed with the receptor five times. The plate is kept for one hour at 37° C. covered with an adhesive foil and thereafter 50 µl of IgE B11 at a concentration of 1500 pM is pipetted into each well of the incubation plate and mixed five times. The respective concentrations are as follows: 5% DMSO, 50 µM substance, 600 mM NaOH, 200 pM receptor, 500 pM IgE; 4; 2; 1; 0.5; and 0.25 nM IgG BSW17.

The plate is sealed with an adhesive foil and incubated for three hours at 37° C. Thereafter 100 µl are transferred from the incubation plate into the streptavidin covalent plate which is kept overnight at 4° C. After a five times wash 100 µl of anti IgE-POD [1:2000] are added and the plate is incubated for another hour at room temperature. The plate is washed again five times and 100 µl of TMB-substrate are added. After 20 minutes incubation at room temperature the reaction is stopped by addition of 100 µl of 4 N $H_2SO_4$ and the plate is read at $^{450}/_{690}$ nm.

Results:

FIG. 2 depicts the functional properties of the FcεRIα receptor at 20 nM IgE. The receptor concentration of 200 pM chosen for the screening assay represents the high endpoint of the exponential phase of the curve. Previous experiments showed that the molar binding ratio for IgE is 1:2.5 and hence 500 pM was chosed as the assay concentration for IgE. The IgG BSW17 standard provides a measure for the sensitivity of the assay system as well as a gauge for the determination of the IC50.

Abbreviations:

B11=recombinant human IgE monoclonal antibody (protein concentration 1850 µg/ml; molecular weight 188 kDa)
BSA=bovine serum albumin
BSW17=IgG monoclonal antibody directed against the $CH_3$ epitope of native IgE (protein concentration 2.3 mg/ml; molecular weight 150 kDa)
CU=chronic urticaria
DMF=dimethylformamide
DMSO=dimethylsulfoxide
EDTA=ethylene diamine tetraacetic acid
ELISA=enzyme-linked immunosorbent assay
FCS=fetal calf serum
FPLC=forced pressure liquid chromatography
IgE=immunoglobulin E
LC=long chain spacer arm
mAb=monoclonal antibody
Mwt=molecular weight
PBS=phosphate-buffered saline
PBSTi=phosphate-buffered saline/Tween 20
POD=horse radish peroxydase
TMB=tetramethylbenzidine
WB=Western blot

BRIEF DESCRIPTION OF THE DRAWINGS

1. Couple streptavidin covalently onto ELISA plates
2. Mix biotinylated FcεRIα-chain and substance solution
3. Incubate
4. Add IgE, incubate and transfer preformed complex onto ELISA plate
5. Wash the plate free of unbound compounds
6. Add detecting antibody (peroxidase-linked anti-human IgE) and incubate
7. Wash and develop with peroxidase substrate

I) Serum specimens are reacted with an anti-IgE mAb and thereafter incubated with biotinylated rsFcεRIα;

II) IgE is blocked, α-chain specific IgG can bind to its antigen;

III) IgG anti-FcεRIα/rsFcεRIα$_{biot}$ complexes bind to the streptavidin-coated plate and are detected with enzyme-coupled anti-human IgG.

Figure 4B:
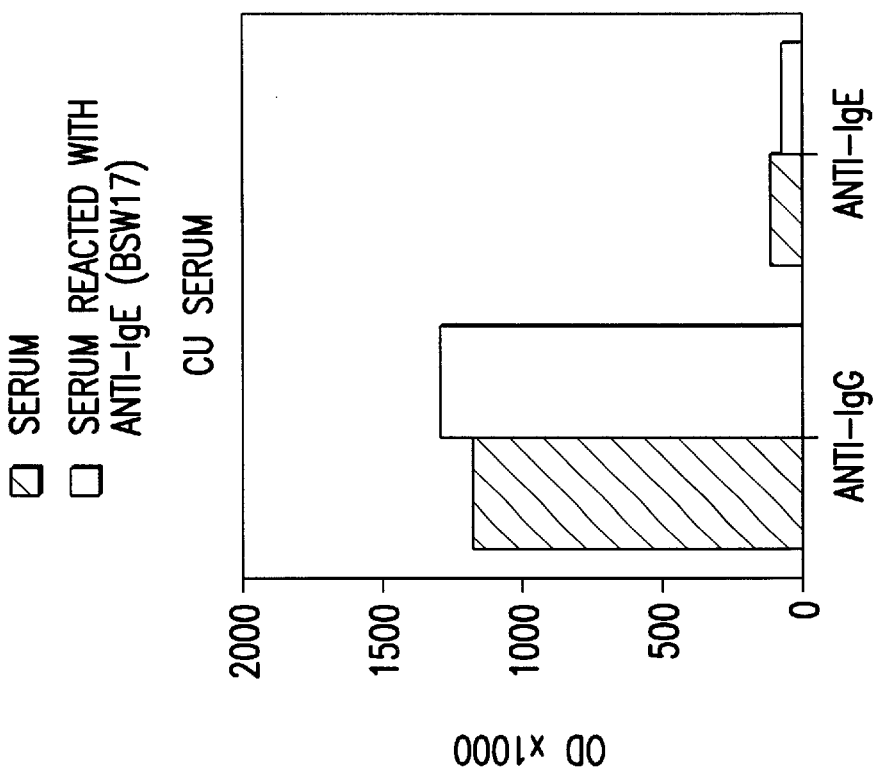
Figure 4A:
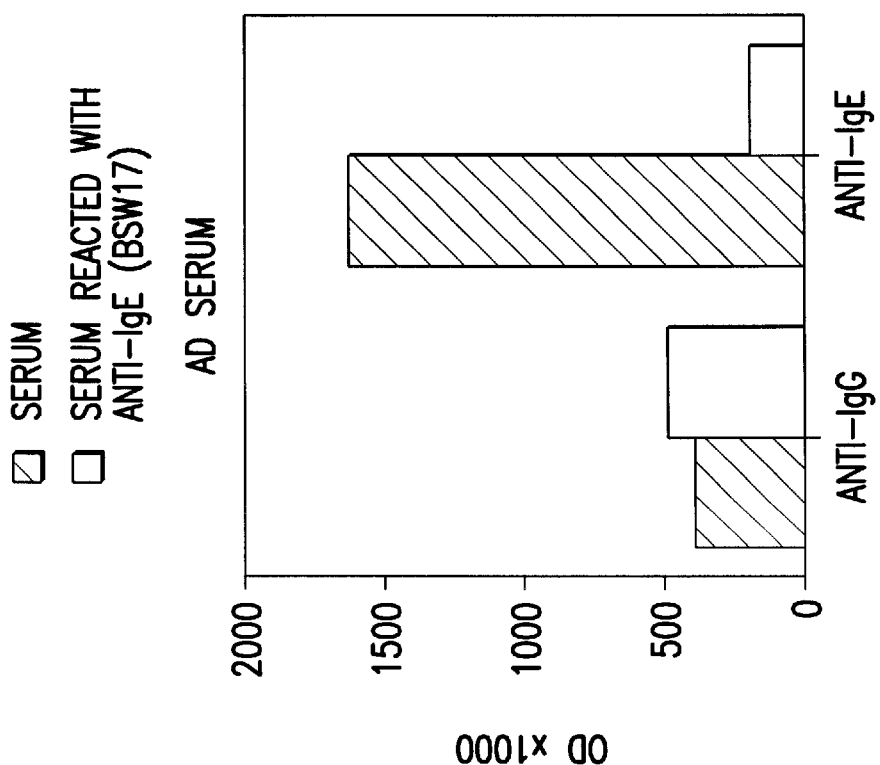

FIG. 4: mAb BSW17 inhibits IgE binding to rs FcεRIα.

Sera (diluted 1:15) from atopic patients (AD) and from chronic urticaria patients (CU) were analyzed for anti-IgG and anti-IgE reactivity with rsFcεRIα in the presence (closed bars) or absence of the anti-IgE mAb BSW17 (dotted bars). y-axis shows dilution-corrected optical density (OD×1000).

▨=serum; ■=serum reacted with anti-IgE (BSW17).

FIG. 5:

(A) Preincubation of streptavidin-coated plates with anti-FcεRIα non-reactive sera does not block the reactivity of IgG anti-FcεRIα reactive sera. Reactivity of two positive and one negative specimen is shown.

(B) Increasing concentrations of randomly selected serum do not affect the detectability of anti-FcεRIα autoantibodies.

(C) Reactivity of autoantibodies to biotinylated rsFcεRIα is blocked by preincubation with unlabeled rsFcεRIα protein but not by preincubation with rhesus monkey papilloma virus (rRhPVL.1).

Figure 6:
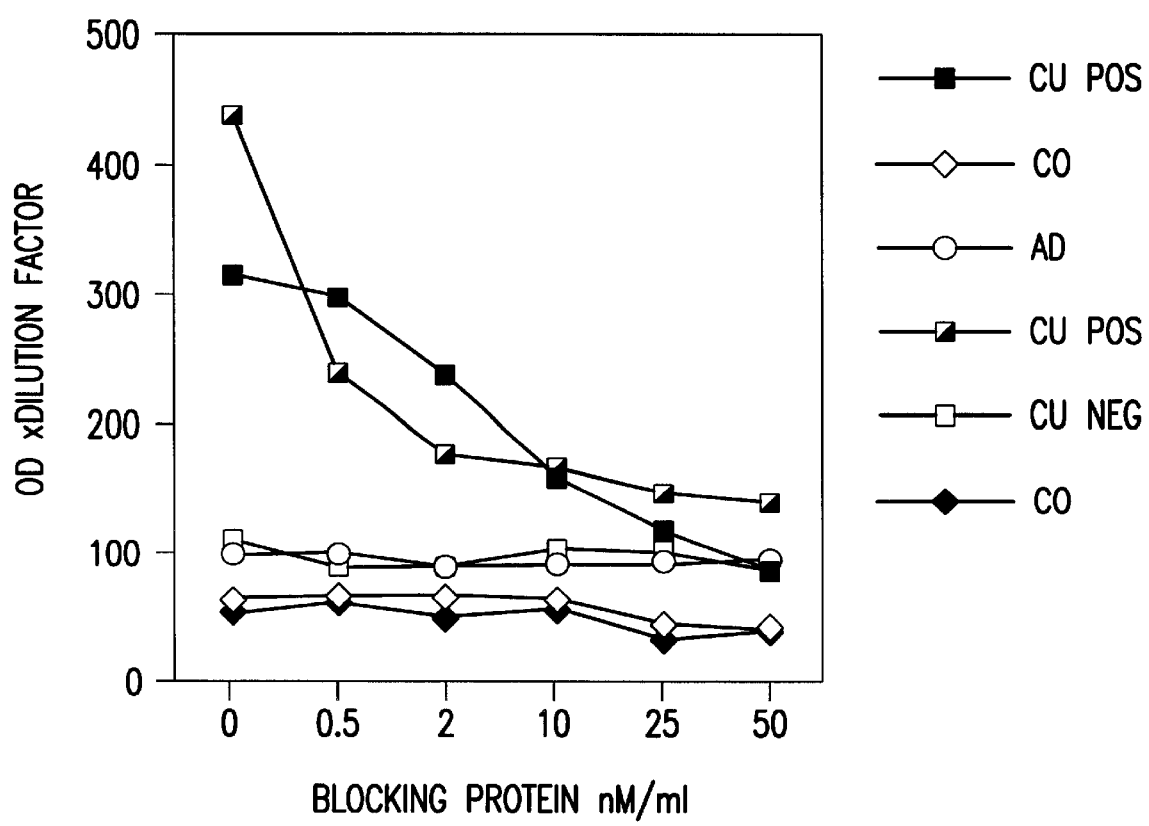

FIG. 6: Unlabeled rsFcεRIα-chain protein was added up to 100-fold higher concentration than the biotinylated receptor (x-axis). Results with serum from anti-FcεRIα-reactive and non-reactive chronic urticaria patients (CU), from atopic dermatitis patients (AD) and from healthy controls (CO) are depicted. The y-axis shows the optical density multiplied by the dilution factor.

Figure 7:
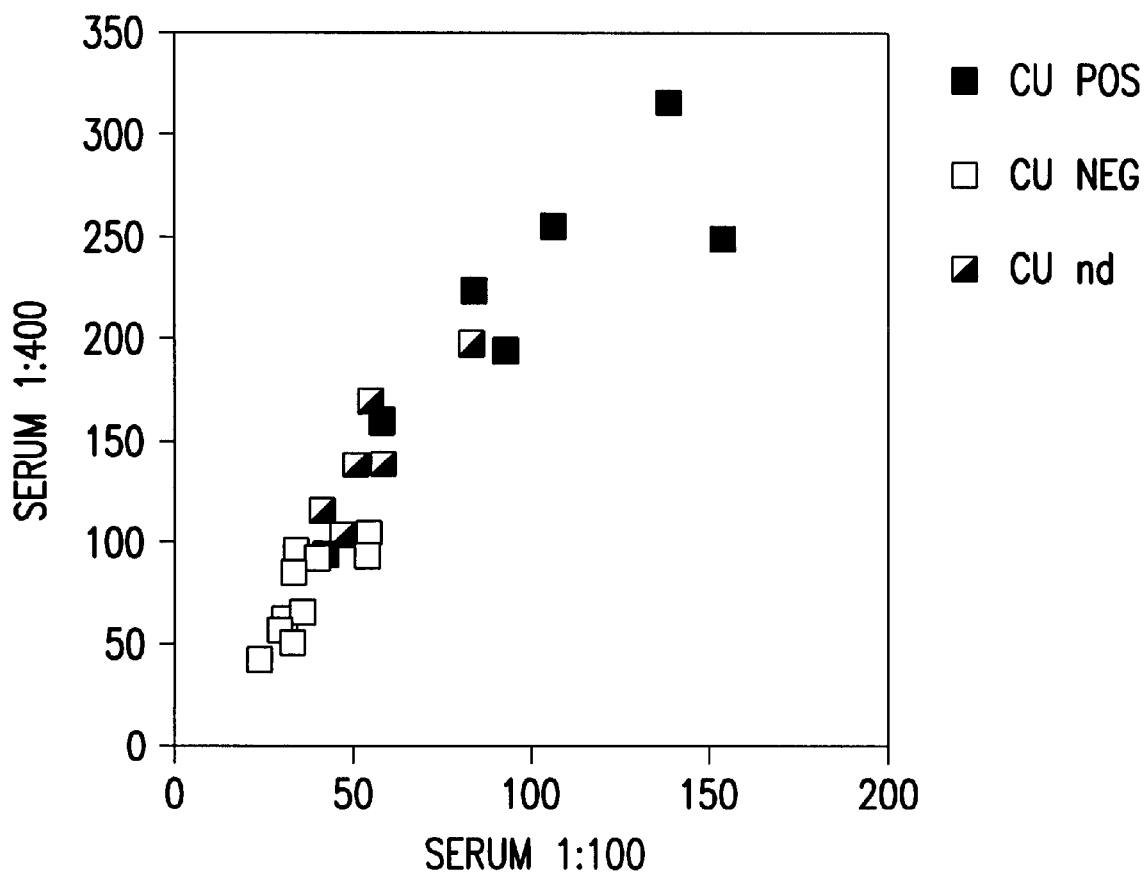

FIG. 7: Correlation of anti-FcεRIα reactivity in Western blot analysis and ELISA. Western blot-reactive (CU pos), Western blot non-reactive (CU neg), and sera that could not be defined by blotting analysis (CU nd) were analyzed in 1:100 (x-axis, OD×100) and 1:400 (y-axis, OD×400) dilution.

Figure 8:
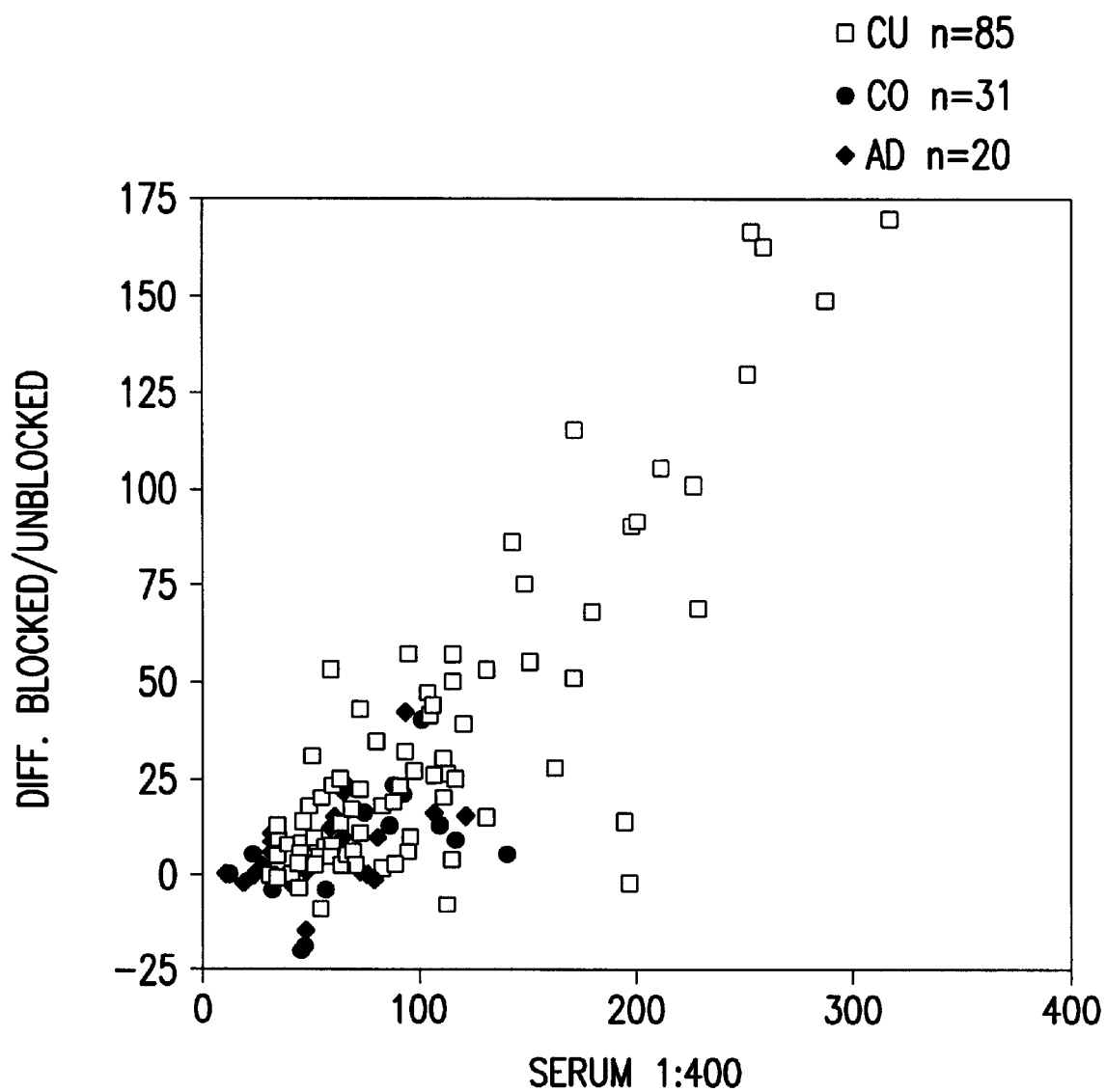

FIG. 8: Sera from 85 chronic urticaria patients (CU), 20 atopic dermatitis patients (AD) and 31 healthy controls (CO) were analyzed for the presence of anti-FcεRIα autoantibodies by ELISA. Reactivity is defined as optical density at a 1:400 dilution (x-axis) versus the rsFcεRIα-blockable reactivity (y-axis).

Materials:

TMB stock solution: 2 mg TMB/ml ethanol, filtered through a glass sinter filter no. 2;
TMB working solution; 100 ml citrate buffer pH 5 plus 2.2 ml TMB stock solution plus 560 μl 0.3% $H_2O_2$:
Wash buffer: PBSdef. with 0.05% TWEEN 20;
Blocking solution: Wash buffer with 2% BSA;
Incubation buffer: Wash buffer with 2% FCS;
rec human IgE receptor: R1α[470 μg/ml] EN 24/460, Mwt 32 kDa;
human IgE: B11 [1850 μg/ml]; Mwt 188 kDa;
biotinylated human IgE receptor: FcεRIα-LC-Biotin Pool 5 [120 μg/ml] Mwt 32 kDa;
PBSdef. pH 9: PBSdef. titrated to pH 9 with 2 M NaOH;
Citrate buffer pH 5: 10 mM (0.86 g citric acid+1.74 g sodium citrate per liter); 10 mM EDTA (3.7 g per liter);
Stop solution: 4 N sulfuric acid;
Streptavidin solution: 2 mg/ml distilled water;
IgG BSW17 [2.3 mg/ml] Mwt 150 kDa.

FURTHER DESCRIPTION OF THE PREFERRED EMBODIMENTS

In a preferred embodiment of the invention this assay method is useful for the differential analysis between autoimmune disorders and classical allergies, i.e. allergies triggered by exogenous factors.

Urticaria is a common disorder characterized by the eruption of transitory, itchy skin swellings that are frequently associated with the occurrence of debilitating and potentially life-threatening angioedema. Although accurate data on the prevalence of urticaria are not available, it is estimated that 15% to 32% of the general population experience urticarial/angio-edematous symptoms during their life time. In about 25% of these patients the initially sporadic character of this condition is followed by a chronic disease period with symptoms of frequent but unpredictable occurrence. If widespread wheals tend to appear daily or almost daily for at least six weeks the disease is termed chronic urticaria (CU). Taken together, CU is a frequent disease afflicting a considerable proportion of the population in the Western hemisphere.

Although it is a well known fact that histamine release from mast cells is of central pathophysiological relevance for the elicitation of CU, the causative agent(s) that mediate mast cell activation remained obscure until very recently. The existence of autoantibodies directed against the high affinity IgE receptor FcεRI in the serum of CU patients was shown. These autoantibodies were found to cross-link FcεRI on basophils and mast cells, resulting in the exocytosis of histamine by these cells. Using recombinant soluble FcεRIα as a reaction target for autoantibodies, it was found that about 37% of CU sera exhibited IgG autoreactivity against FcεRIα. No IgG anti-FcεRIα reactivity was observed in the serum of atopic dermatitis patients or healthy control individuals. Therefore, IgG autoreactivity against FcεRIα is of central pathophysiological importance for CU and furthermore is a selective marker identifying an autoimmune-mediated sub-entity of this disease. It is hence of great interest to develop strategies that allow the reliable and fast detection and quantification of such serum autoantibodies.

A further indication of the urgent need for an appropriate screening system comes from the fact that up to now laborious and cost-intensive searches for certain implicated, but not unequivocally proven, etiopathogenetic conditions, e.g. bacterial or fungal infections, hormonal dysregulation, psychological factors, neoplasms, and intolerance to certain food activities. are performed in most CU patients. It is obvious that such laboratory, physical, and psychological examinations, which often require long-lasting hospitalization of the patients. cause enormous financial expense. Thus, the quick and easy detection of disease-eliciting autoantibodies helps to drastically reduce the requirement for diagnostic procedures that are unrevealing in most patients.

Design of an Anti-FcεRIα ELISA System:

1. Expression and Purification of Human Recombinant Soluble FcεRIα

The gene segment encoding the extracellular portion of human FcεRIα is cloned into the baculovirus vector pVL941 (BACULOGOLD Transfection Kit no. 21100 K, Baculovirus Vector PVL1392/1393 no. 21201 P, PharMingen, D-22335 Hamburg, Germany). Recombinant baculovirus is generated in insect cells using the BACULOGOLD transfection kit (PharMingen) according to the manufacturer's instructions. The soluble receptor molecule is purified from supernatants of infected insect cells by a two step chromatography protocol. First, the material is immunoaffinity-purified on a Sepharose 4B (Pharmacia Biotech)—coupled mouse anti-human FcεRIα mAb (E. Fiebiger et al., *J. Clin. Invest.* 96 [1995] 2606–2612). Final purification is achieved by anion exchange column chromatography. The purification product migrates as a single 32 kD band as judged by silver staining of a denaturing polyacrylamide gel.

2. Insect Cell-Expressed Recombinant Soluble FcεRIα (rsFcεRIα) as a Reaction Target for IgG Anti-FcεRIα Autoantibodies Solid-phase immobilization of soluble FcεRIα on ELISA plates leads to a significant reduction of its capacity to bind IgE. This effect is most likely due to changes in the tertiary structure of rsFcεRIα induced by the hydrophobic interactions of the protein with the solid phase matrix. Therefore, conventional ELISA conditions are inappropriate for the detection of serum IgG anti-FcεRIα autoantibodies. To circumvent this problem, an ELISA system is established that allows the binding of autoantibodies to native, non-denatured rsFcεRIα in a liquid phase. Such a strategy mimics the natural binding conditions of serum IgG anti-FcεRIα autoantibodies with their target in vivo. Hence, a defined molar concentration of biotinylated rsFcεRIα is allowed to react with diluted serum specimens, an aliquot of this reaction mixture is then transferred to a streptavidin-bound ELISA plate and the binding, of IgG anti-FcεRIα/rsFcεRIα complexes is monitored using peroxidase-coupled anti-human IgG antibodies.

3. Mouse mAbs Directed Against the Fc Part of Human IgE are Required to Eliminate the Interfence of Serum IgE with rsFcεRIα

Figure 1:
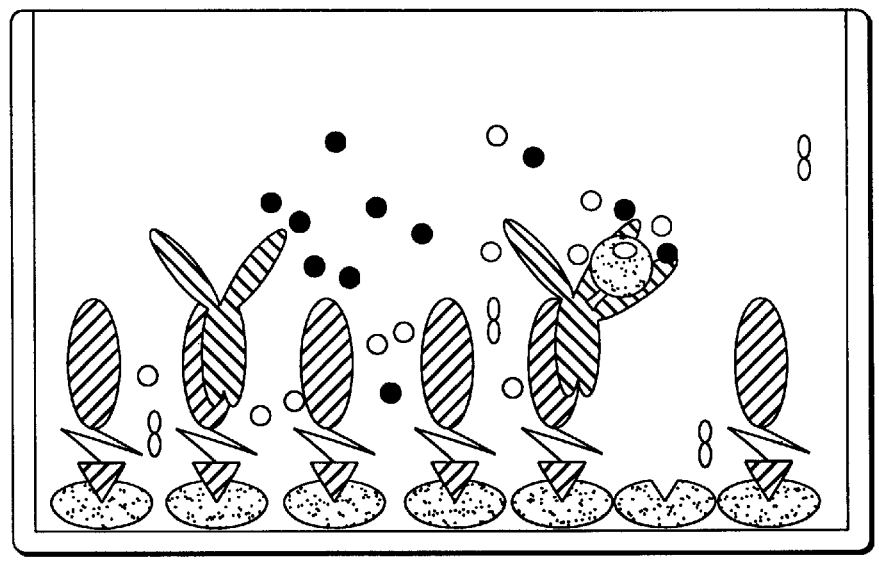
FIG. 1: Key steps of assay.
Figure 1:
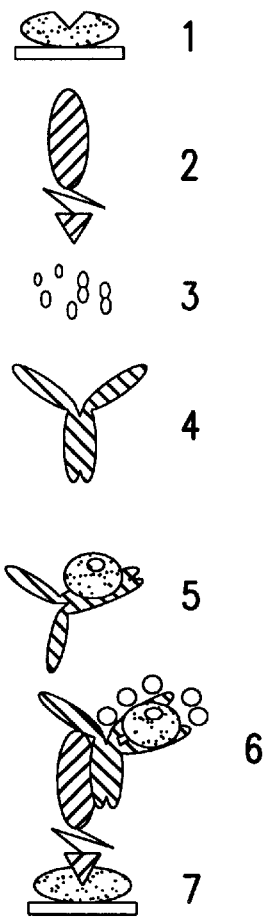
Figure 2:
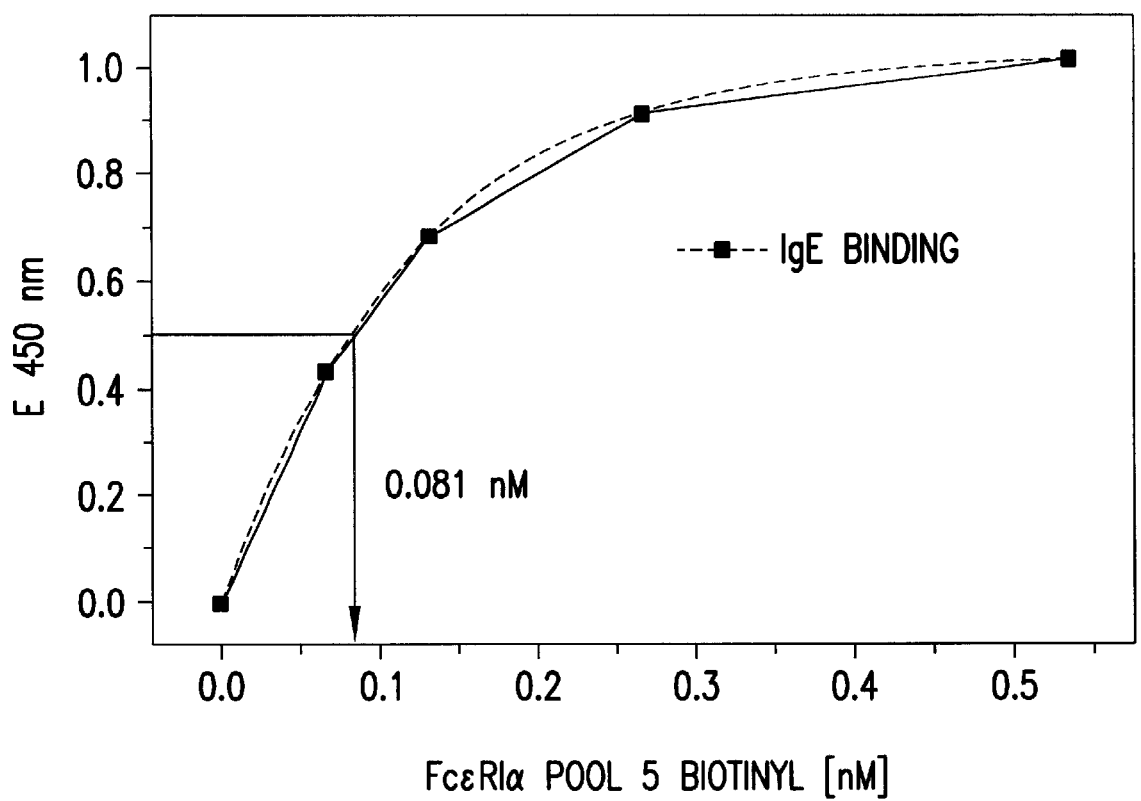
FIG. 2: Binding capacity of FcεRIα at 20 nM IgE ■=IgE binding
Figure 3A:
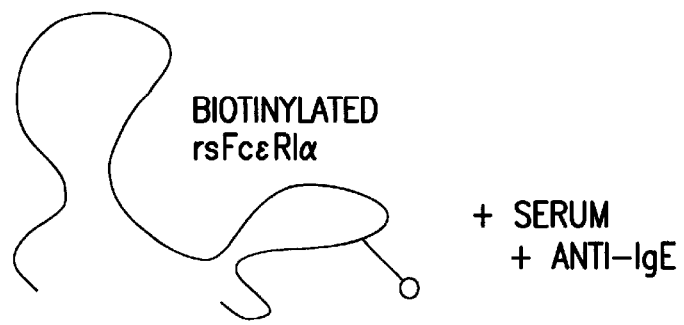
FIG. 3: Scheme of the anti-FcεRIα ELISA.
Figure 3B:
Figure 3C:
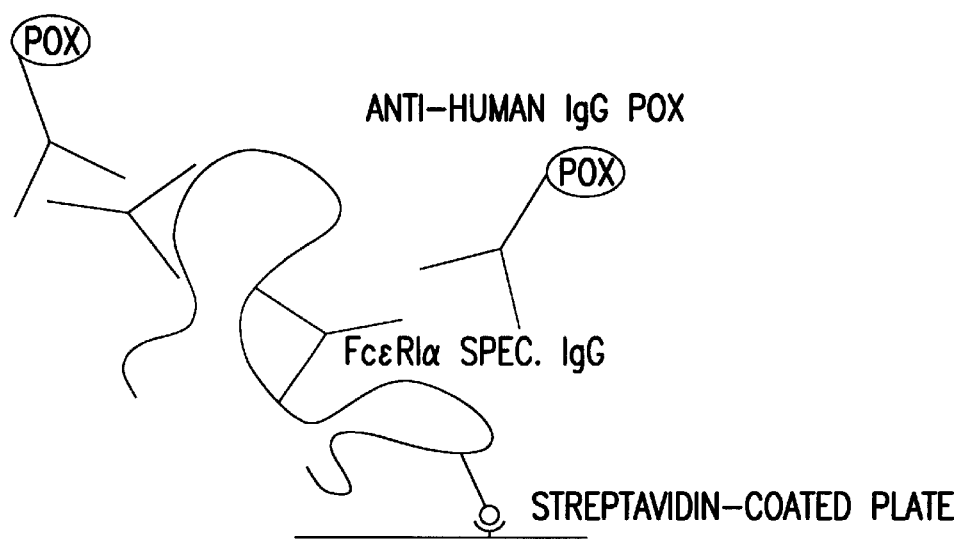

Serum IgE binds rsFcεRIα and therefore can (I) competitively inhibit autoantibody-binding to rsFcεRIα and/or (II) allow the binding of naturally occurring IgG anti-IgE antibodies to rsFcεRIα. To avoid this IgE-mediated interference with the ELISA system, sera are preincubated with mouse mAbs directed against the Fe part of human IgE prior to their exposure to biotinylated rsFcεRIα. Using the anti-IgE mAb BSW17 a complete blockage of serum IgE binding to rsFcεRIα is observed. Importantly, preincubation of sera with this mAb does not at all influence the binding of serum IgG anti-FcεRIα to rsFcεRIα. Therefore, mAb BSW17 is routinely added to the serum specimens prior to the analysis. Scheme of the ELISA method is given in FIG. 3.

4. Methodology

Serum dilutions (1:100; 1:400) are incubated with 2 nM mAb BSW17 for at least 3 hours at room temperature. Thereafter, half of the sample volume is removed and incubated with non-biotinylated rsFcεRIα overnight at 4° C. All samples are then reacted with 5 nM biotinylated rsFcεRIα for 3 hours at 37° C. 100 μl aliquots of these reaction mixtures are transferred to ELISA plates covalently coupled to streptavidin and incubated for 1 hour at room temperature. After several rounds of washings, plates are reacted with peroxidase-coupled anti-human IgG F(ab')$_2$ (1:10000) or anti-human IgE. The amount of plate-bound enzyme was evaluated using TMB.

5. Results mAb BSW17 blocks the interference of serum IgE with soluble recombinant FcεRIα. In order to apply serum rather than purified serum IgG for routine diagnostics of IgG anti-FcεRIα autoreactivity, the possible interference of serum IgE with the ELISA system had to be eliminated. Therefore, the anti-human IgE mAb BSW17 was tested for its ability to block IgE binding to rsFcεRIα. Serum from atopic dermatitis (AD; containing >10$^4$ U IgE) and from chronic urticaria (CU) patients were analyzed for their IgE and IgG reactivity with rsFcεRIα in the presence or absence of mAb BSW17. As depicted in FIG. 4, preincubation of AD sera with BSW17 abolished the rsFcεRIα-bound IgE reactivity. In contrast, the rsFcεRIα-bound IgG reactivity of CU sera was not affected by mAb BSW17. Virtually identical results were obtained when BSW17-exposed sera were used in immunoblotting experiments or when 2 other anti-IgE mAbs were used. Taken together, these results show that preincubation of sera with BSW17 abrogates the possible interference of serum IgE and thus should allow the detection of IgG anti-FcεRIα autoantibodies in unfractionated serum samples.

Specificity of the rsFcεRIα-Based ELISA Detection System

Figure 5A:
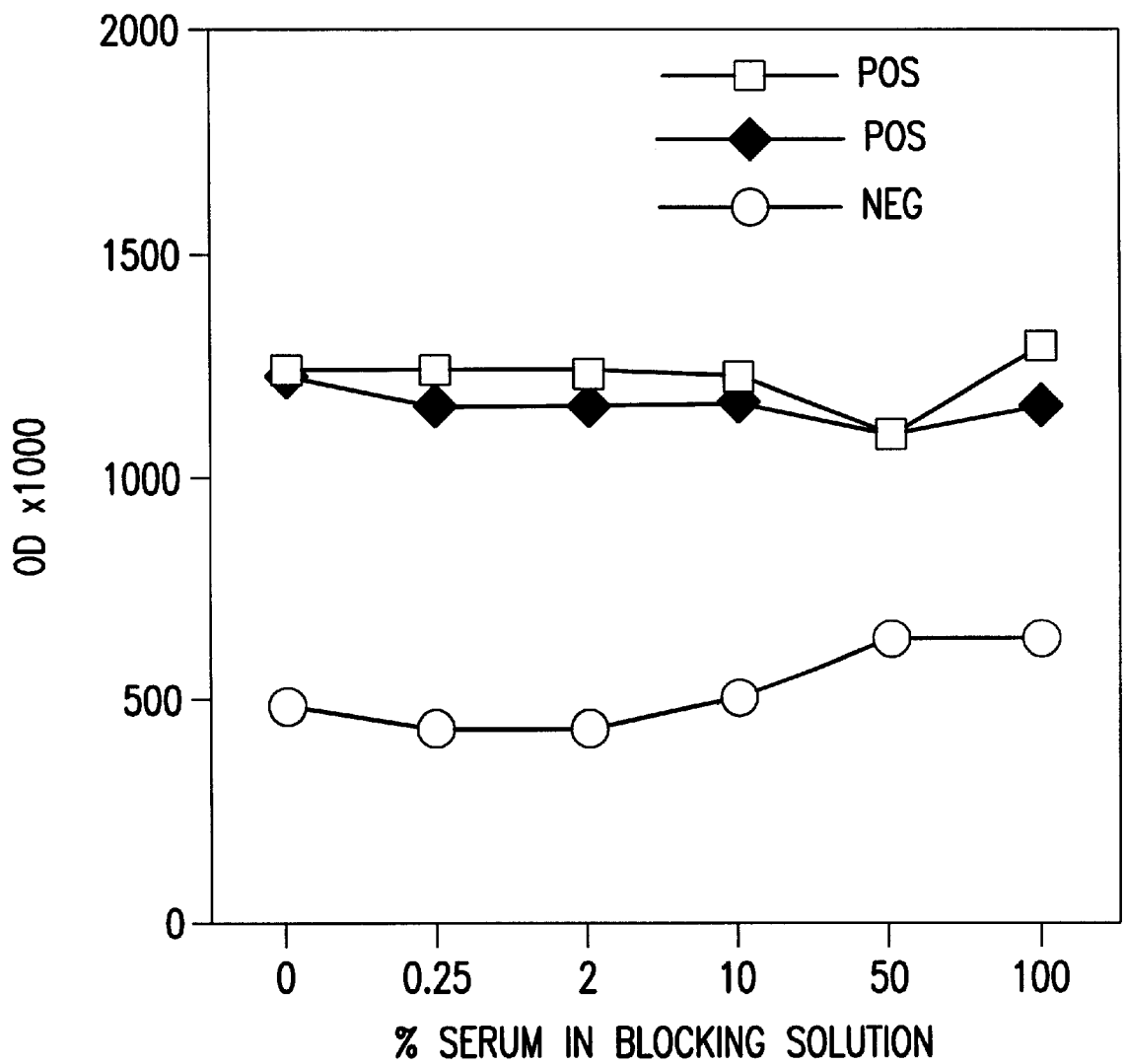
Figure 5B:
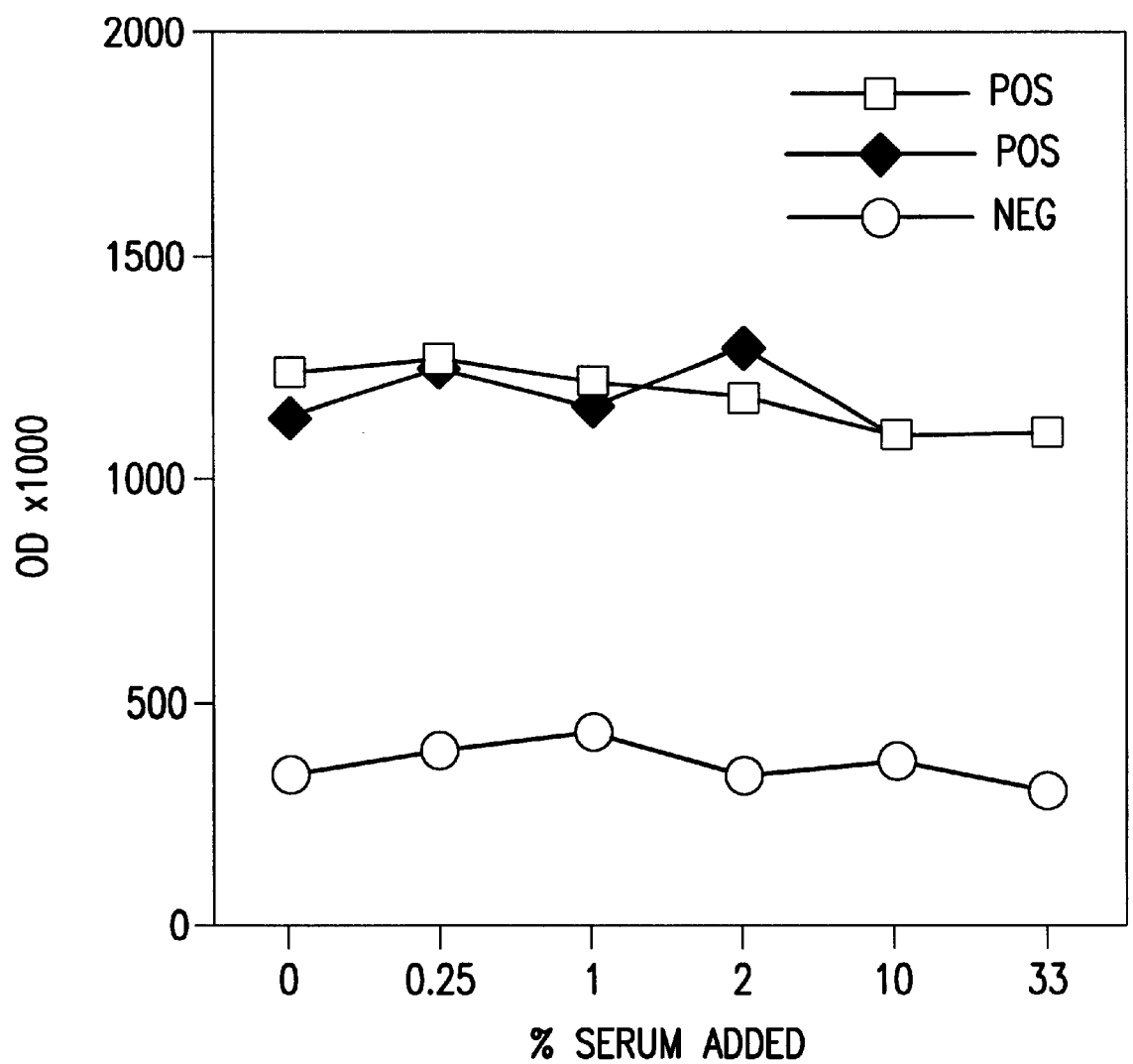
Figure 5C:
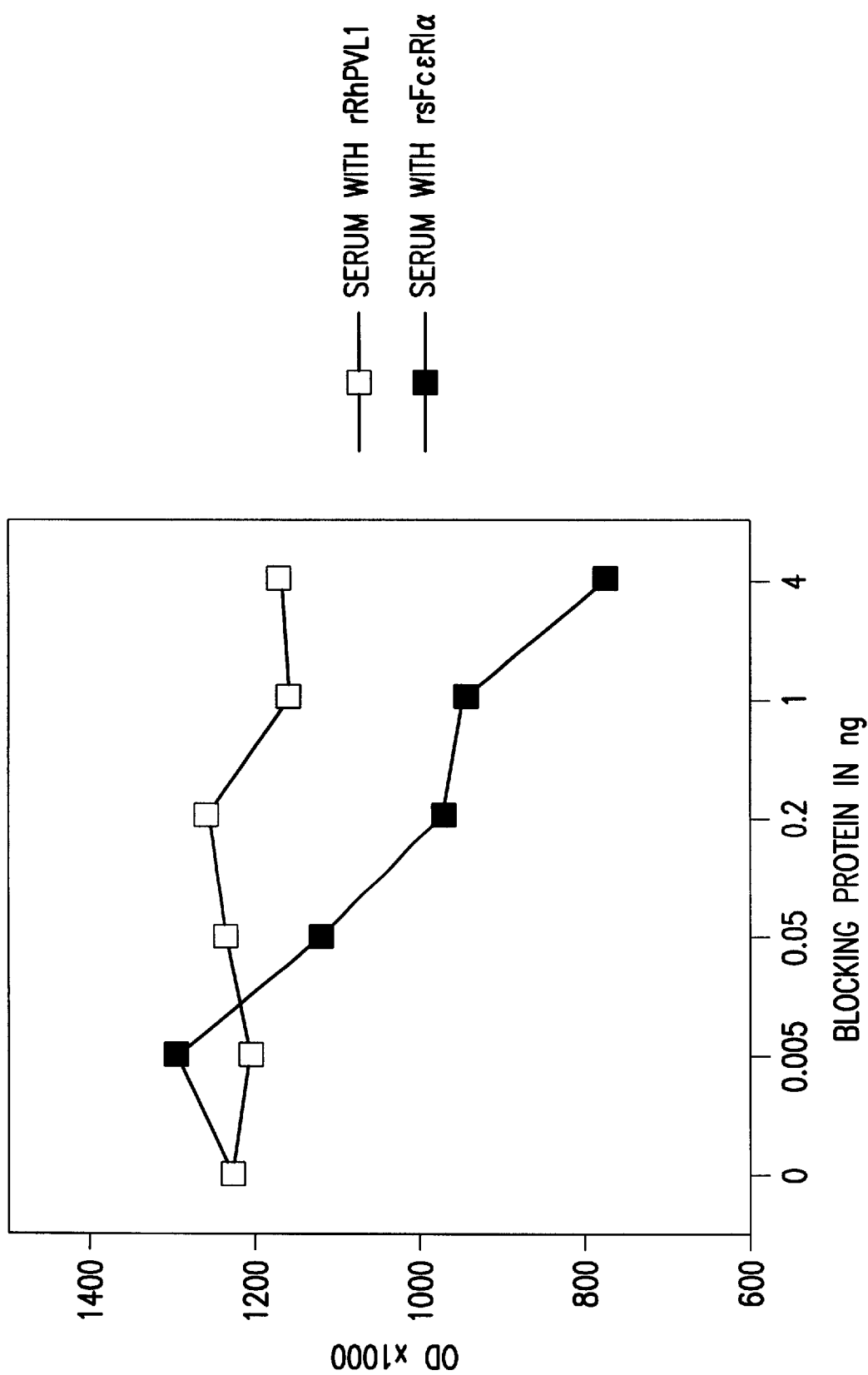

Next it was investigated whether (i) serum biotin, (ii) the serum IgG concentration, or (iii) insect cell-expressed recombinant proteins other than rsFcεRIα can interfere with the ELISA detection of IgG anti-FcεRIα autoantibodies. (I) Preincubation of streptavidin-coated plates overnight with various concentrations of healthy donors' serum neither quantitatively nor qualitatively affects the detectability of autoantibodies (FIG. 5A). However, incubation with pure serum results in stronger signals, explainable by enhanced background. Nevertheless, the possibility that soluble serum-derived biotin may inhibit IgG anti-FcεRIα/rsFcεRIα complex-binding to streptavidin-coated ELISA plates can be ruled out. (ii) When increasing concentrations of irrelevant (i.e., IgG anti-FcεRIα-negative sera) are mixed with autoantibody-containing sera no influence on the detectability of IgG anti-FcεRIα autoantibodies is observed (FIG. 5B). This indicates that this system allows the reliable detection of autoantibodies irrespective of the IgG concentrations of the serum specimen tested. (iii) In order to test the antigen specificity of this ELISA test system. sera with various concentrations of rsFcεRIα or e.g. recombinant L1 protein of rhesus monkey papilloma virus (rRhPV) are preincubated prior to analysis. The experiments reveal that selectively rsFcεRIα but not rRhPV can inhibit the interaction of serum IgG anti-FcεRIα autoantibodies with biotinylated rsFcεRIα (FIG. 5C). These findings give an additional proof for the specificity of this test system and exclude that the observed reactivity is due to serum IgG reactivity to insect sugar components. In further studies, non-biotinylated rsFcεRIα protein in concentrations equimolar to those of biotinylated rsFcεRIα was applied.

Results obtained indicate that the ability to block ELISA reactivity by high concentrations of rsFcεRIα can be used to discriminate IgG anti-FcεRIα autoantibody-containing and non-containing serum samples. Thus, besides the OD value reflecting the IgG-binding to the ELISA plates, the ability to block this reactivity by non-labeled RsFcεRIα is a valuable indicator for the presence of IgG anti-FcεRIα autoantibodies (FIG. 6).

Correlation of Results Obtained in Western Blot (WB) and ELISA Analysis

The comparative analysis of results obtained in WB studies and ELISA experiments reveals good correlation between these two methods. FIG. 7 shows that WB-reactive sera also exhibit ELISA reactivity in 7 out of 8 cases. None of the WB-negative samples shows reactivity in the ELISA detection system. Sera that cannot be classified in WB due to high background staining, show either weak or no reactivity in the ELISA indicating that these specimens may contain low titer autoantibody levels not discernible in WB analysis.

Patient Study

In an extended patient study the presence of IgG anti-FcεRIα autoreactivity in 85 patients suffering from chronic urticaria and 20 atopic dermatitis patients versus 31 healthy controls was evaluated. Results are shown in FIG. 8. IgG anti-FcεRIα autoreactivity is found predominantly if not exclusively in the group of CU patients.

What is claimed is:

1. An assay for high capacity screening for substances that interfere with the binding of human IgE to its high affinity receptor FcεRIα comprising
    admixing a solution containing a substance to be tested with dissolved, biotinylated Fcε RIα receptor to form a mixture;
    admixing the mixture with IgE to form a binding reaction mixture;
    transferring the binding reaction mixture to a streptavidin-coated multiple well plate; and
    detecting whether the substance to be tested interferes with binding of IgE to biotinylated Fcε RIα receptor in the binding reaction mixture by means of an enzyme-labeled antibody raised against human IgE.

2. A method for the differential analysis between autoimmune disorders and allergies triggered by exogenous factors in a patient, a serum sample having been obtained from the patient, comprising determining if IgG that bind to the Fcε RIα receptor are present in the serum sample from the patient by:
    admixing the serum sample with dissolved, biotinylated Fcε RIα receptor to form a binding reaction mixture;
    transferring the binding reaction mixture to a streptavidin-coated multiple well plate; and
    detecting the presence of IgG that bind to the biotinylated Fcε RIα receptor in the binding reaction mixture by means of an enzyme-labeled antibody raised against human IgG, wherein the presence in the patient serum sample of IgG that bind to the biotinylated Fcε RIα receptor indicates that the patient is suffering from an autoimmune disorder rather than an allergy triggered by exogenous factors.

3. The method of claim 2, which further comprises, prior to determining if IgG that bind to the FcεRIα receptor are present in the serum sample from the patient, the step of preincubating the serum sample from the patient with an anti-IgE antibody.

4. The method of claim 3, wherein said anti-IgE antibody is the antibody BSW17 produced by the hybridoma cell line deposited with the European Collection of Animal Cell Cultures under the provisions of the Budapest Treaty on the deposit of microorganisms under deposit number 96121916.

* * * * *

UNITED STATES PATENT AND TRADEMARK OFFICE
CERTIFICATE OF CORRECTION

PATENT NO. : 6,258,549 B1
DATED : July 10, 2001
INVENTOR(S) : Auer et al.

Page 1 of 1

It is certified that error appears in the above-identified patent and that said Letters Patent is hereby corrected as shown below:

Title page,
Column 1,
Line 18, change "Anal.kBio-" to -- Anal. Bio- --.
Line 22, change "Immonol." to -- Immunol. --.

Column 2,
Line 2, change "Immonol." to -- Immunol. --.

Signed and Sealed this

Second Day of April, 2002

*Attest:*

*Attesting Officer*

JAMES E. ROGAN
*Director of the United States Patent and Trademark Office*